United States Patent [19]

Pacelli

[11] Patent Number: 4,766,622
[45] Date of Patent: Aug. 30, 1988

[54] PERITONEAL WASTE DISCHARGE SYSTEMS

[76] Inventor: Alphonso Pacelli, 246 Rte. 46 West, Totowa, N.J. 07512

[21] Appl. No.: 28,736

[22] Filed: Mar. 23, 1987

[51] Int. Cl.⁴ .................... A47K 17/00; A61M 31/00
[52] U.S. Cl. ............................................ 4/661; 4/300; 4/300.2; 4/663; 4/664; 604/277; 604/317; 604/334
[58] Field of Search ............... 4/661, 663, 662, 300.2, 4/239, 341, 420, 434, 312, 556, 560, 578, 590; 640/277, 334, 317, 905; 134/100

[56] References Cited

U.S. PATENT DOCUMENTS

| | | | |
|---|---|---|---|
| 2,438,073 | 3/1948 | Saur | 4/661 X |
| 2,568,857 | 9/1951 | Jacobs | 4/239 |
| 2,664,573 | 1/1954 | Taylor | 4/661 |
| 2,700,773 | 2/1955 | Colendar | 4/300.2 |
| 2,864,094 | 12/1958 | Williams, Jr. | 4/611 |
| 4,134,404 | 1/1979 | Williams, Jr. | 4/661 X |
| 4,285,076 | 8/1981 | Dickstein | 4/341 |

Primary Examiner—Henry K. Artis
Attorney, Agent, or Firm—Melvin K. Silverman

[57] ABSTRACT

Disclosed is a peritoneal waste discharge system including a disinfectant storage chamber, a measuring chamber in selectable fluid contact with the storage chamber, a discharge cup in selectable contact fluid with the measuring chamber, a peritoneal bag vertically oriented above the discharge cup, and a conduit having the discharge cup as an input and having a bowl of a conventional toilet as an output. The disinfectant discharge chamber, the peritoneal waste bag, and the conduit are all in alignment with the gravity vector.

1 Claim, 1 Drawing Sheet

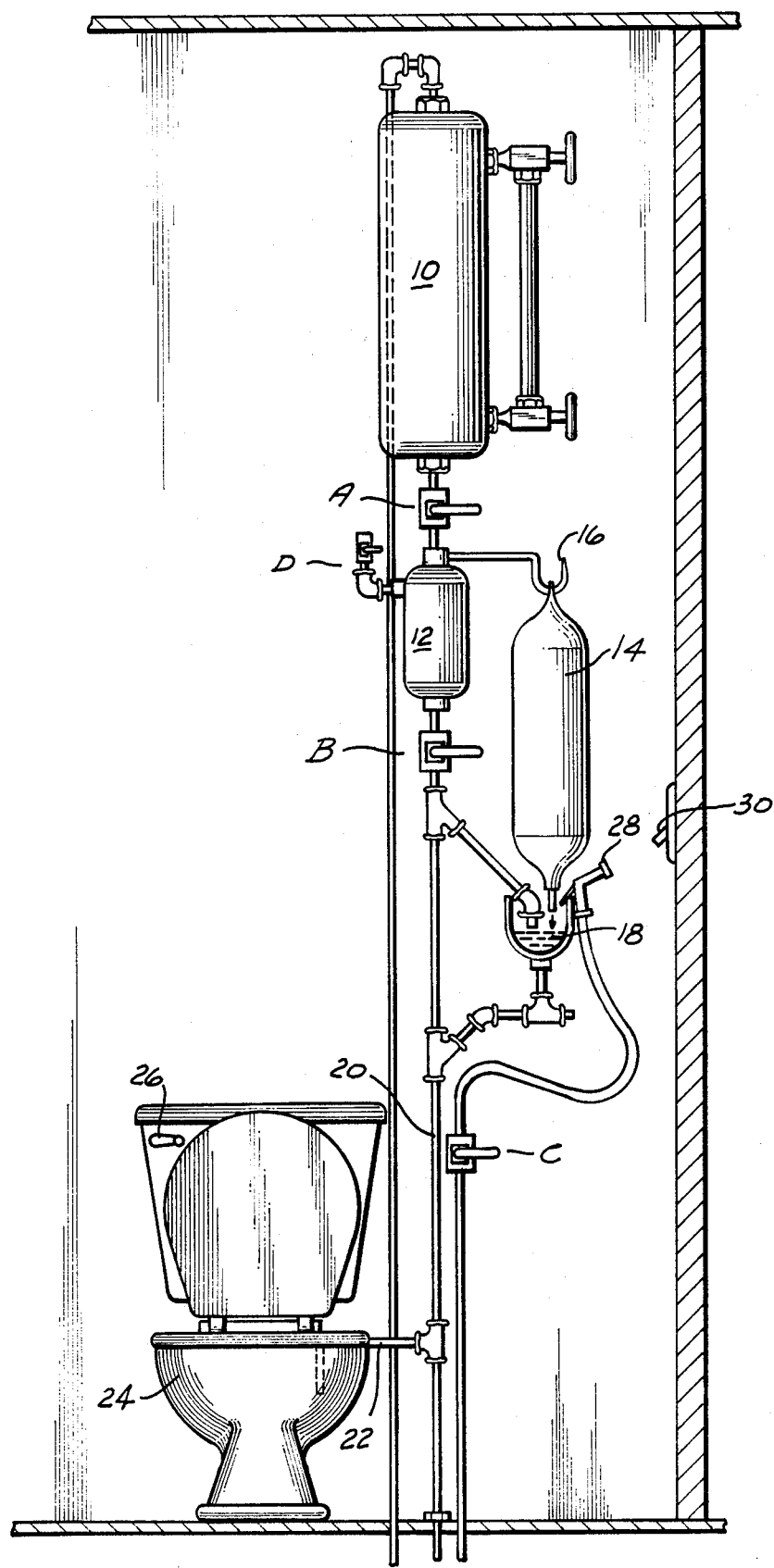

PERITONEAL WASTE DISCHARGE SYSTEMS

BACKGROUND OF THE INVENTION

Users of peritoneal, ileostomy, and other such bags involving drainage from internal organs into an external compartment are confronted with the problem of how to dispose of the contents of such compartments in a sanitary and convenient fashion. The same is equally a problem to those caring for individuals who must use such a facility.

The simple dumping of a peritoneal or ileostomy bag into a toilet is not satisfactory solution in that that procedure has been found to be unsanitary, permitting germs and the like to escape in the process of dumping or flushing into a conventional toilet.

The need has long existed for an arrangement for an apparatus that would facilitate disposal of such bags in a convenient, sanitary fashion. Efforts in the prior art to address this problem are extremely limited. To the knowledge of the inventor, such prior art efforts, as best known to him, are reflected in U.S. Pat. No. 4,285,076 (1981) to Dickstein, entitled Flushing Apparatus for Ileostomy Bag; and U.S. Pat. No. 4,345,343 (1982) to Shipman, entitled Apparatus for the Cleaning and Sanitation of a Restroom or Lavatory. Somewhat further removed is prior art reflected in U.S. Pat. No. 2,568,857 (1951) to Jacobs, entitled Colostomy Toilet and U.S. Pat. No. 2,700,773 (1955) to Colendar, entitled Hospital Plumbing Arrangement.

None of the above efforts reflect a system as convenient or as sanitary as might be desired. For example, the above reference to Dickstein requires the use of rubber gloves while said reference to Jacobs requires that the individual, or nurse therefor, must still empty the bag manually.

The reference to Shipman is appropriate only for hospital use and cannot be applied to the home area, such being the use for which the instant invention is contemplated. The reference to Colander involves the simple addition of a T-joint to an otherwise conventional toilet arrangement and does not address the problems solved by the inventor's system.

SUMMARY OF THE INVENTION

The invention relates to a peritoneal waste discharge system including a disinfectant storage chamber, a measuring chamber in selectable fluid contact therewith, a discharge cup in selectable contact fluid with said measuring chamber, a peritoneal bag vertically oriented above said discharge cup, and conduit means having said discharge cup as an input and having a bowl of a conventional toilet as an output. The disinfectant discharge chamber, peritoneal waste bag, and said conduit means are all in alignment with the gravity vector.

The apparatus enables the simultaneous mixing of a disinfectant such as bleach with the contents of the peritoneal bag such that, through such conduit means, the solution of waste material and disinfectant may be flushed down a conventional toilet upon depressing on the flush handle thereof.

It is an object of the present invention to provide a convenient, sterile method of disposing of peritoneal and related waste stored within a body fluid bag.

It is another object to provide an improved, home-care flushing means for peritoneal and related waste bags.

It is a further object to provide a system of the above type requiring a minimum of handling and potential contamination to a user or a nurse during the course of home care.

The above and other objects and advantages of the present invention will become apparent from the hereinafter set forth Detailed Description of the Invention, the claims, and the Drawings appended herewith.

BRIEF DESCRIPTION OF THE DRAWING

The FIGURE is a schematic system view of the inventive waste discharge system.

DETAILED DESCRIPTION OF THE INVENTION

There is provided an external reservoir (not shown) which serves as a master holding tank for a disinfectant such as bleach. Therefrom, through the use of either a pump, siphon, or combination thereof, the disinfectant is conveyed to a storage chamber 10. Below said tank is provided a ball valve A the purpose of which is to permit the filling of a measuring chamber 12, which may be provided with a site glass (not shown), for checking the fluid level. The use of such a measuring chamber is necessary to insure that the correct amount of disinfectant will be provided to the system upon each occasion of usage thereof.

Below measuring chamber 12 is provided a ball valve B.

After a peritoneal (or other) waste discharge bag 14 has been positioned upon hook 16, the bag 14 is allowed to empty into discharge cup 18. Ball valve B is then opened to permit the disinfectant in measuring chamber 12 to also empty into discharge cup 18.

From cup 18, the gravity vector will pull the combination of the contents of discharge bag 14 and the disinfectant from measuring chamber 12 through conduit 20, into conduit 22, and therefrom into bowl 24 of the toilet. As bowl 24 is reached, handle 26 of the toilet is depressed such that the material flowing from conduit 22 will be flushed down the toilet bowl 24 in an otherwise conventional fashion.

After the above is achieved, nozzle 28, which serves a rinse function, is employed through the actuation of valve C which is a supply of fresh water. Thereby, nozzle 28 can be used to rinse discharge cup 18.

Thereafter, measuring chamber 12 is refilled through the actuation of ball valve A so that the system is ready for its next usage.

It is noted that valve D serves a bleed function by allowing air to go into the measuring chamber after the measuring cup has been emptied. This will permit measuring chamber 12 to be easily refilled when valve A is turned to the open position.

As may be noted in the FIGURE, there is further provided a pump switch means 30, the function of which is to pump disinfectant from the external reservoir into chamber 10 when the same becomes necessary.

It is to be appreciated that the above system enables the ready disposal by users in the peritoneal, ileostomy, and colostomy areas, to conveniently and sterilely dispose of the contents without need for handling, or without the need for the use of gloves because of the much reduced possibility of contamination with the present system.

It is thereby to be appreciated that the present system is of particular utillity in the home care or home nursing area.

Accordingly, while there has been shown and described the preferred embodiment of the present invention, it will be understood that the invention may be embodied otherwise than as herein specifically illustrated or described and that within said embodiments certain changes in the detail and construction, and the form of arrangement of the parts may be made without departing from the underlying idea or principles of this invention within the scope of the appended claims.

I claim:

1. A waste container discharge system, for use in combination with a toilet, comprising:
   (a) a disinfectant storage chamber located near the ceiling of a room;
   (b) a measuring chamber in selectable fluid communication with said storage chamber and beneath said storage chamber with reference to the gravity vector;
   (c) first valve means located medially between said storage chamber and said measuring chamber, said valve means defining said selective fluid communication, wherein filling of said measuring chamber to a desired quantity of disinfectant may be accomplished by said first valve means;
   (d) hook means for holding a body fluid bag in vertical, gravity-drain position;
   (e) cup means, above the level of said toilet, disposed proximal to the mouth of said fluid bag and beneath an output of said measuring chamber;
   (f) second valve means located medially between said measure-chamber and the output thereof, wherein said second valve may be selectably opened to permit flow of the contents of said measuring chamber into said cup means at the time said fluid bag is drained thereinto; and
   (g) conduit means for fluidly communicating the output of said cup means to a bowl of said toilet, whereby the flush lever of said toilet will be depressed as the contents of said conduit means reaches said bowl.

* * * * *